US00PP13451P2

(12) United States Plant Patent
Olesen et al.

(10) Patent No.: US PP13,451 P2
(45) Date of Patent: Jan. 7, 2003

(54) FLORIBUNDA ROSE PLANT NAMED 'POULDAHLE'

(76) Inventors: L. Pernille Olesen, Hillerødevejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 24 days.

(21) Appl. No.: 09/774,822

(22) Filed: Jan. 30, 2001

(51) Int. Cl.[7] ..... A01H 5/00
(52) U.S. Cl. ..... Plt./148
(58) Field of Search ..... Plt./148, 141, 144, Plt./130, 137, 133

*Primary Examiner*—Bruce R. Campell
*Assistant Examiner*—June Hwu

(57) ABSTRACT

A new floribunda garden rose plant which has abundant, light pink to peach flowers and attractive foliage. This new and distinct variety has shown to be uniform and stable in the resulting generations from asexual propagation.

1 Drawing Sheet

SUMMARY OF THE INVENTION

Botanical: *Rosa hybrida* 'POULdahle'.

Commercial: Floribunda.

The present invention constitutes a new and distinct variety of garden rose plant which originated from a controlled crossing between 'St. Helena' (CANlish) and an 'unnamed seedling', both unpatented varieties. The two parents were crossed during the summer of 1993 and the resulting seeds were planted in a controlled environment in Fredensborg, Denmark. The new variety is named 'POULdahle'.

The new rose may be distinguished from its seed parent, 'St. Helena', by the following combination of characteristics:

1. 'POULdahle' is more free-flowering than the seed variety.
2. 'POULdahle' has soft pink to peach flowers, while 'St. Helena' has lilac pink flowers.
3. 'POULdahle' exhibits thicker and more glossy foliage than 'St. Helena'.

The new variety may be distinguished from its pollen parent, 'an unnamed seedling' by the following combination of characteristics:

1. 'POULdahle' contains more flowers per plant when compared to the pollen parent.
2. 'POULdahle' exhibits thicker and more glossy foliage than the pollen parent.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULdahle' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULdahle' was selected in the spring 1994 by the inventors as a single plant from the progeny of the aforementioned hybridization.

Asexual reproduction of 'POULdahle' by traditional budding and rooted cuttings was first done by L. Pernille and Mogens N. Olesen in their nursery in Fredensborg, Denmark in August, 1994. This initial and other subsequent asexual propagations conducted in controlled environments have demonstrated that the characteristics of 'POULdahle' are true to type and are transmitted from one generation to the next.

BRIEF DESCRIPTION OF THE DRAWING

The accompanying color illustration shows as true as is reasonably possible to obtain in color photographs of this type 'POULdahle', potted rose plant. Specifically illustrated in SHEET 1 are 'POULdahle's' foliage, flower buds, partially opened buds, and open blooms.

DETAILED DESCRIPTION OF THE VARIETY

The following is a description of 'POULdahle', as observed in a nursery in Jackso County, Oreg., on plants aged nine months. Color references are made using The Royal Horticultural Society (London, England) Colour Chart, 1995, except where common terms of color are used.

For a comparison, several physical characteristics of the rose variety 'POULskov', a rose variety from the same inventors described and illustrated in U.S. Plant Pat. No. 9,062 and issued on Feb. 28, 1995 are compared to 'POULdahle' in Chart 1.

CHART 1

| | 'POULdahle' | 'POULskov' |
|---|---|---|
| Color of open flower, innermost petals, middle zone. | Red Group 56D | Red Group 49D-56B |
| Petalage | Semi-double | Very double |
| Upon opening color basal petal spot, outer side | Yellow Group 8C | Yellow-Green Group 154D to Yellow Group 4D |

Parents:
*Seed parent.*—'St. Helena'.
*Pollen parent.*—'Unnamed seedling'.

FLOWER AND FLOWER BUD

Blooming habit: Continuous.
Flower bud:
*Bud form.*—Ovate.
*Size.*—25 mm long and 30 mm wide.
*Color.*—As sepals unfold, Orange Group 29D.
*Sepals.*—Size: 8 mm (w)×11 mm (l) Color, upper surface: Yellow-Green Group 144A. Lower surface: Weak foliaceous appendages on three of the five sepals. Color, lower surface: Green Group 138B. Anthocyanin present, colored Greyed-Red Group 178A. Texture, upper surface: Slightly pubescent. Stipitate glands present on sepal margins. Texture, lower surface: Slightly pubescent.
*Receptacle.*—5 mm (l)×8 mm (h). Surface: Smooth. Color: Yellow-Green Group 144A.
*Peduncle.*—Surface: Moderate abundance of hairs and prickles. Color: Yellow-Green Group 144A. Strength: Strong. Length: 40 to 50 mm average length.
*Borne.*—Singularly. Very few to few flowering shoots.
Flower bloom:
*Fragrance.*—Weak.
*Size.*—Average flower diameter is 100–120 mm when open.
*Form.*—Shape of flower when viewed from the side: Upper part: Flat. Lower part: Flat. Viewed from above: Irregularly rounded.
*Petalage.*—Semi-double. Average range: 18–20 petals under normal conditions.
*Duration.*—8 to 10 days. Blooms are self-cleaning.
Color:
*Petals.*—Inner Side: Middle zone: Red Group 56D. Marginal zone: Red Group 56D. Basal petal spot: Yellow Group 8B–C. Outer side: Middle zone: Red Group 56D. Marginal zone: Red Group 56D. Basal petal spot: Yellow Group 8C.
General tonality: On open flower Red Group 36B to Orange Group 29D. No change in the general tonality at the end of the 5th day.
Petals:
*Petal reflex.*—Somewhat reflexed.
*Undulation of margin.*—Weak to medium.
*Size.*—35 mm (l)×30 mm (w).
*Quantity.*—18 to 20.
*Thickness.*—Average.
*Petaloids.*—5 to 8 petaloids. Petaloids are, on average, 15 mm long and 10 mm wide. Coloration on both upper and lower surfaces of petaloids is Red Group 56D. Petaloid surface texture is smooth.
Reproductive organs:
*Pollen.*—Color: Yellow-Orange Group 17A. Quantity: Average.
*Anthers.*—Size: 4 mm long. Color: Yellow Group 1D. Quantity: Approximately 20–25.
*Filaments.*—Color: Yellow-Green Group 145C and D. Length: 10 mm.
*Stigmas.*—Slightly superior in location to anthers. Color: Greyed-White Group 157A.
*Styles.*—Color: Greyed-White Group 157B. Quantity: 30 to 40.
*Seed formation.*—Hips: Not observed.
*Pistils.*—Length: 20 mm long. Quantity: 25–30.

PLANT

Plant growth: Moderate, upright to bushy. When grown as a budded field grown plant on *Rosa multiflora* understock, the average height of the plant is 60–80 cm and the average width is 60 cm.
Stems:
*Thorns.*—Incidence: 4 thorns per 10 cm of stem. Size: Average length is 8 mm. Shape: Linear. Color: Yellow-Green Group 146C.
Plant foliage:
*Leaf size.*—40 mm (l)×30 mm (w).
*Glossiness.*—Medium glossiness.
*Color.*—Upper Leaf Surface: Green Group 137A. Lower Leaf Surface: Green Group 128B. Juvenile foliage: Upper Leaf Surface: Yellow-Green Group 144A. Lower Leaf Surface: Green Group 128B. Anthocyanin intonation: Present on upper and lower surface leaflet margins, sepal tips, peduncles, and petioles. Color: On juvenile foliage, Greyed-Red Group 181B.
Plant leaflets:
*Leaflet.*—Cross Section: Slightly concave. Margin Undulation: Weak to medium. Thickness: Moderately thick. Size: 13 mm (l)×10 mm (w). Venation: Reticulate. Edge: Serrated. Apex: Acute. Base: Rounded.
*Stipules.*—Size: 7 mm (w)×23 mm (l). Color: Yellow-Green Group 144B. On plants grown under high light conditions, stipules may exhibit intonations of Greyed-Red Group 181A. Stipitate glands: Present on edges of stipules. Anthocyanin: Greyed-Red Group 181A.
*Petiole.*—Length: 10 mm. Color: Yellow-Green Group 144C. Underneath: Yellow-Green 144A. Margins: Yellow-Green Group 144A. Texture: Smooth. Anthocyanin: None noted.
*Rachis.*—Color: Yellow-Green Group 144C. Underneath: Yellow-Green 144A; one thorn present. Margins: Yellow-Green Group 144A. Texture: Smooth.
Disease resistance: Above average resistance to mildew, rust, black spot, and Botrytis under normal growing conditions in Jackson County, Oreg.
Cold hardiness: The variety 'POULdahle' has been found to be resistant to damage from cold in USDA Zone 7.

We claim:

1. A new and distinct variety of rose plant of the Floribunda rose class, substantially as herein illustrated and described as a distinct and novel rose variety due to its abundant light pink to peach flowers, disease resistance, and extended period of bloom.

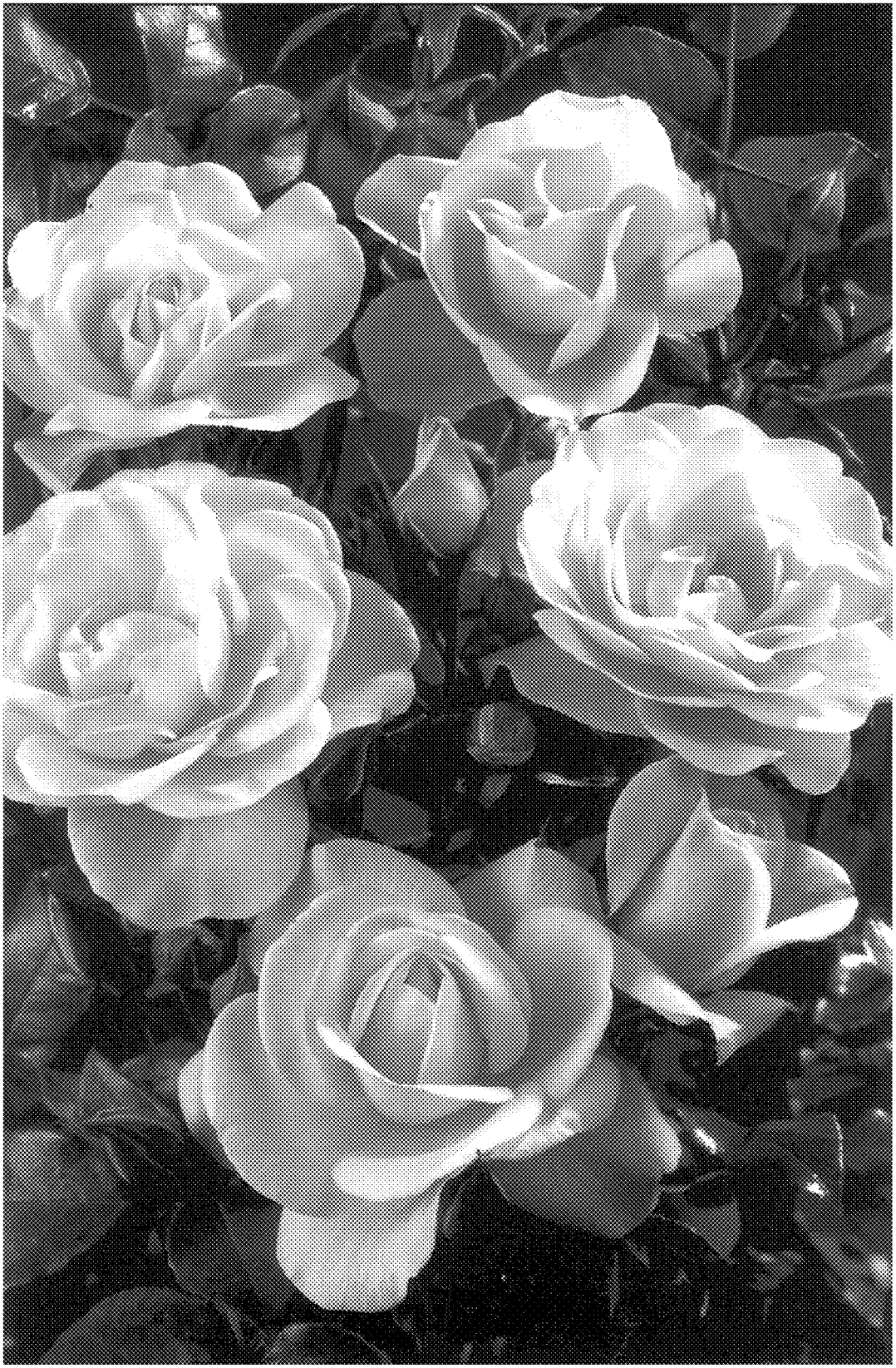

* * * * *